US007579163B2

(12) United States Patent
Eriksen et al.

(10) Patent No.: US 7,579,163 B2
(45) Date of Patent: Aug. 25, 2009

(54) METHOD OF FERMENTATION (75) Inventors: Henrik Eriksen, Stavanger (NO); Kurt Strand, Stavanger (NO); Lars Jørgensen, Stavanger (NO)

(73) Assignee: STATOIL ASA, Stavanger (NO)

( * ) Notice: Subject to any disclaimer, the term of this patent is extended or adjusted under 35 U.S.C. 154(b) by 307 days.

(21) Appl. No.: 10/486,694

(22) PCT Filed: Aug. 16, 2002

(86) PCT No.: PCT/GB02/03798

§ 371 (c)(1),
(2), (4) Date: Jul. 9, 2004

(87) PCT Pub. No.: WO03/016460

PCT Pub. Date: Feb. 27, 2003

(65) Prior Publication Data

US 2004/0241790 A1    Dec. 2, 2004

(30) Foreign Application Priority Data

Aug. 16, 2001  (GB) ................... 0120025.2
Apr. 18, 2002  (GB) ................... 0208906.8

(51) Int. Cl.
    *C12N 1/20*     (2006.01)
    *C12P 1/00*     (2006.01)
(52) U.S. Cl. ..................... 435/41; 435/252.1
(58) Field of Classification Search .............. 435/41, 435/252.1
    See application file for complete search history.

(56) References Cited

U.S. PATENT DOCUMENTS 4,498,910 A * 2/1985 Benkmann ............... 95/100

6,492,135 B1 * 12/2002 Larsen .................... 435/41

FOREIGN PATENT DOCUMENTS

| CN | 85109440 A | 7/1987 |
| EP | 0 306 466 | 3/1989 |
| EP | 0 339 356 | 11/1989 |
| EP | 0 418 187 | 3/1991 |
| WO | WO 00/70014 | * 11/2000 |
| WO | WO 00 70014 | 11/2000 |
| WO | WO 01 60974 | 8/2001 |

OTHER PUBLICATIONS

CN-85109440A, Published Jul. 8, 1987, Inventor YAn et al. (English Translation from Chinese).*

* cited by examiner

*Primary Examiner*—Jon P Weber
*Assistant Examiner*—Kailash C Srivastava
(74) *Attorney, Agent, or Firm*—Sughrue Mion, PLLC (57) ABSTRACT

The invention provides a process for the production of biomass by culturing a microorganism in an aqueous liquid culture medium circulating in a loop reactor having an effluent gas removal zone where from carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen is introduced into the reactor and mixed with the liquid culture medium therein, characterised in that oxygen introduction in said nutrient gas introduction zone is effected at a plurality of locations along the flow path through said loop reactor at a rate such that the average dissolved oxygen content of said liquid culture medium measured using a polarographic oxygen electrode does not exceed 25 ppm.

19 Claims, 4 Drawing Sheets

Loop reactor inner surface

FIG. 4

METHOD OF FERMENTATION

CROSS-REFERENCE TO RELATED APPLICATION

This application is a 371 of PCT/GB02/03798, filed Aug. 16, 2002; the disclosure of which is incorporated herein by reference.

This invention relates to improvements in and relating to processes for fermenting microorganisms, e.g. for the generation of biomass or the preparation of materials produced by microorganisms, and to fermentor apparatus for the performance thereof, in particular processes for culturing microorganisms in a loop reactor using a gaseous nutrient.

Recently, much attention has been directed toward the development of new sources of protein which may be incorporated into foods for human and/or animal consumption. A number of different protein-containing materials have been proposed as substitutes for more traditional sources of protein, such as fish meal, soya products and blood plasma, in human foods and as animal feeds. These materials include single-cell microorganisms such as fungi, yeasts and bacteria which contain high proportions of proteins. These may be grown by reproduction producing biomass through the growth of the microorganisms on hydrocarbon or other substrates. Today, the most widely used protein-containing microorganisms (also referred to herein as "single-cell proteins") are those derived from fungi or yeast.

Single-cell protein materials can be used directly in foods, e.g. as a spray dried product, or the biomass may be further processed, e.g. by hydrolysis and/or separation, before use.

Besides being simply used as sources of biomass, microorganisms may be grown and harvested to serve as sources of useful chemicals, e.g. drug compounds, proteins, carotenoids, etc. Thus for example Du Pont in WO 02/18617, WO 02/20815, WO 02/20728 and WO 02/20733 (the contents of which are hereby incorporated by reference) describe the use of methanotrophic bacteria, and in particular Methylomonas 16a ATCC PTA 2402), for the preparation of carotenoids.

In DK-B-170824 (Dansk Bioprotein A/S) and in WO01/60974 (Norferm DA), the contents of both of which are hereby incorporated by reference, is described a loop reactor for use in cultivating microorganisms to generate biomass, e.g. for culturing methanotrophic bacteria to generate a material which can for example be used in or as or as a precursor to human or animal feed.

The loop reactor described in DK-B-170824 has a top unit connected to a conduit having, in order, a down-flow section, a substantially horizontal flow section, an up-flow section and a non-vertical out-flow section. The top unit is cylindrical with its axis vertical and with the down-flow section of the conduit attached to its base. The out-flow section of the conduit extends tangentially from a side of the top unit. In this way, effluent gas and liquid culture medium entering the top unit from the out-flow section may be separated efficiently with the gas being withdrawn from the headspace of the top unit and the liquid being returned to the down-flow section of the conduit. The aqueous liquid culture medium is driven around the reactor loop, with gaseous and non-gaseous nutrients (e.g. oxygen, methane, nitrogen sources and minerals) being introduced into the conduit and mixed with the liquid culture medium therein, with biomass-containing culture medium being withdrawn from the conduit, and with effluent gas (e.g. carbon dioxide-containing gas) being withdrawn from the top unit. Nutrient addition and effluent gas withdrawal is generally continuous, while biomass withdrawal may be continuous or batchwise.

In the loop reactor described in DK-B-170824 the circulation rate of the reaction medium was generally about 30 to 90 seconds per circuit. Since unconsumed oxygen and methane in the effluent gas would make this potentially explosive and would be uneconomical since oxygen and methane would be wasted, gaseous nutrient addition could not occur at all points along the conduit. Likewise, to ensure efficient separation of carbon dioxide from the liquid reaction medium for venting from the top unit, gas/liquid mixing could not be effected at all points along the conduit either. In practice therefore, in the loop reactor of DK-B-170824, gaseous nutrient addition was such that the dissolved oxygen content in the culture medium would drop to about zero by the time the culture medium reached the top of the upflow section of the conduit.

However, while the loop reactor described in DK-B-170824 can be successfully used for biomass production, when used at high biomass concentrations (e.g. above 5 g/L) the production process is susceptible to occasional sudden failure, requiring the process to be restarted with fresh live bacteria.

We have now found that this problem may be reduced or avoided if nutrient gases (e.g. methane and/or oxygen, particularly oxygen) are supplied into the conduit so as to reduce the time the culture medium is essentially free of an essential nutrient and/or so as to avoid or minimize periods of unduly high concentrations of nutrient gases in the culture medium.

Thus in one aspect the invention provides a process for the production of biomass by culturing a microorganism, preferably a methanotrophic bacterium, in an aqueous liquid culture medium circulating in a loop reactor having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen, and preferably also methane, are introduced into the reactor and mixed with the liquid culture medium therein, characterised in that oxygen introduction in said nutrient gas introduction zone is effected at a plurality of locations along the flow path through said loop reactor at a rate such that the average dissolved oxygen content of said liquid culture medium measured using a polarographic oxygen electrode (e.g. in mixer-free sections of the reactor) does not exceed 25 ppm, more preferably 20 ppm, especially 15 ppm, more especially 10 ppm, and preferably also such that the dissolved oxygen content of said liquid culture medium at each said location (with the optional exception of the first said location downstream of said degassing zone) is at least 0.5 ppm, especially at least 1 ppm, more especially at least 3 ppm.

In this aspect of the invention, the oxygen introduction locations are preferably so spaced that the flow time between locations is less than 20 seconds, especially less than 16 seconds, particularly less than 6 seconds, more preferably less than 5 seconds, still more preferably less than 4 seconds, other than between the last and first locations (i.e. those immediately upstream and downstream of the degassing zone).

By average dissolved oxygen content is meant the average along a diameter of the cross sectional plane of the reactor. Where the reactor is not circular in cross section, the term diameter should be understood to mean maximum dimension between inside walls. Such an average may be taken by measuring dissolved oxygen content at several, e.g. 3, 5 or 7, equally spaced points along the diameter.

The dissolved oxygen content should desirably be measured at mixer-free sections of the loop reactor, i.e. places within the reactor where the cross section through the reactor does not pass through a mixer device. Desirably the dissolved oxygen content is measured at mixer-free sections downstream of the oxygen introduction zones and the subsequent mixers.

Thus the dissolved oxygen content of the culture medium is conveniently measured using a polarographic oxygen electrode (available commercially, e.g. from Ingold) at positions between the oxygen introduction locations sufficiently far downstream of the previous such location that mixing of oxygen and culture medium is substantially complete.

In order that oxygen concentration extremes may be avoided on oxygen introduction, introduction is preferably effected through a plurality of apertures at each introduction location, e.g. an array of apertures spaced apart in the plane transverse to the flow direction and optionally also along the flow direction. This may be achieved by dispersing in the reactor multi-armed, perforated gas distributors, preferably with the pressure drop from inside to outside the distributor being up to 6 bar, e.g. 0.4 to 3 bar especially 0.6 to 1 bar. Such distributors are conveniently disposed in the gaps between adjacent static mixer arrays in the reactor. In one preferred embodiment, gas distributors are also disposed within the static mixer arrays, e.g. by disposing perforated tubes along mixer channels or by the use of perforated corrugated panels that function both as gas distributors and as plates within the mixer array. Hollow panel mixer plates through which coolant (e.g. cold water) is flowed may also be used to cool the culture medium in the reactor.

The dissolved oxygen content is preferably measured upstream of each oxygen introduction location with the measured values being fed to a computer arranged to control nutrient introduction rates, cooling, biomass withdrawal, etc. In this way the dissolved oxygen content can be maintained within the desired range throughout the reactor and for extended operation periods.

Desirably, the oxygen content of the culture medium in the effluent gas removal zone, or at the lowest dissolved oxygen concentration point in the loop, is less than 0.1 ppm by weight. This results in the biomass product having greater bioavailability as a feedstuff.

While the dissolved oxygen content of the liquid culture medium may drop to negligible or undetectable levels, i.e. about 0 ppm by weight, it is preferred that it should remain at detectable levels over at least a significant proportion of the path length through the reactor. Thus viewed from a further aspect the invention provides a process for the production of biomass by culturing a microorganism, preferably a methanotrophic bacterium, in an aqueous liquid culture medium circulating in a loop reactor having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen, and preferably also methane, are introduced into the reactor and mixed with the liquid culture medium therein, characterised in that oxygen introduction in said nutrient gas introduction zone is such that between said nutrient gas introduction zone and said degassing zone the dissolved oxygen content of the liquid culture medium does not fall below 3 ppm by weight (preferably at least 4 ppm, especially at least 5 ppm).

Viewed from a still further aspect the invention provides a process for the production of biomass by culturing a microorganism, preferably a methanotrophic bacterium, in an aqueous liquid culture medium circulating in a loop reactor having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen, and preferably also methane, are introduced into the reactor and mixed with the liquid culture medium therein, characterised in that oxygen introduction into said liquid culture medium is so effected that the dissolved oxygen content of said liquid culture medium does not fall below 3 ppm by weight (preferably at least 4 ppm, especially at least 5 ppm) over a path length of the loop reactor corresponding to more than 30 seconds, preferably 20 seconds, more preferably 10 seconds, especially 5 seconds.

Viewed from a yet still further aspect the invention provides a process for the production of biomass by culturing a microorganism, preferably a methanotrophic bacterium, in an aqueous liquid culture medium circulating in a loop reactor having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen, and preferably also methane, are introduced into the reactor and mixed with the liquid culture medium therein, characterised in that oxygen introduction in said nutrient gas introduction zone is such that between said nutrient gas introduction zone and said degassing zone the dissolved oxygen content of the liquid culture medium does not fall below X ppm by weight, where X is defined by $$X = 1.35 \, Y.B$$

where B is the biomass content of the culture medium in g/L and Y is from 0.75 to 1.25, preferably 0.80 to 1.20, especially 0.85 to 1.15, more preferably 0.90 to 1.10, more especially 0.95 to 1.05, and B is greater than 5, especially greater than 10, particularly 15 to 30, especially 18 to 25.

Viewed from a still further aspect the invention provides a process for the production of biomass by culturing a microorganism, preferably a methanotrophic bacterium, in an aqueous liquid culture medium circulating in a loop reactor having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen, and preferably also methane, are introduced into the reactor and mixed with the liquid culture medium therein, characterised in that oxygen introduction in said nutrient gas introduction zone is such that the dissolved oxygen content of the liquid culture medium over at least 30% (preferably at least 50%, more preferably at least 60%) of the path length of the loop reactor is at least 10 ppm by weight, the dissolved oxygen content of the liquid culture medium immediately prior to introduction of said driving gas in said degassing zone is at least 3 ppm by weight (preferably at least 4 ppm, especially at least 5 ppm), and the oxygen content of said effluent gas is at least 1 mole % (preferably at least 2 mole %, e.g. 2 to 8 mole %).

These methods described herein as further aspects of the invention are preferably combined with the method of the invention as first defined.

In the process of the invention, it is preferred to drive the liquid culture medium around the loop reactor using a propeller. It is especially preferred to use a propeller having overlapping or multiple, radially curved blades, i.e. a low-cavitation propeller. Such low-cavitation propellers are well-known in the field of submarine design. By overlapping blades it is meant that at least one line exists that is parallel to the propeller axis and that passes through at least two blades. By a radially curved blade it is meant that there is an angle between the radial lines passing through the base and tip of the blade. The use of such propellers in a loop fermentation reactor is novel and forms a further aspect of the invention. Thus viewed from a further aspect the invention provides a process for the production of biomass by culturing a microorganism, preferably a methanotrophic bacterium, in an aqueous liquid culture medium circulating in a loop reactor (preferably one having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen and preferably also methane are introduced into the reactor and mixed with the liquid culture medium therein), characterised in that said liquid culture medium is circulated through said loop reactor under the action of a propeller having overlapping or multiple, radially curved blades.

Using such low cavitation propellers, it is possible to pump liquids having a greater gas content than with conventional propellers and thus it is possible to have nutrient gases introduced into the liquid culture medium closer upstream of the propeller than is otherwise possible. In this way, the proportion of the reactor path length which has low dissolved gas content may be reduced.

The mixing of the nutrient gases into the liquid culture medium is an important aspect of the performance of the process of the invention. We have found that the use of static mixers, each comprising an array of mixer plates, positioned downstream of nutrient gas injection points results in a particularly efficient dissolution of the nutrient gases even though the gas:liquid volume ratio is relatively small. Such use of mixer plate arrays in loop fermentation reactors is novel and forms a further aspect of the invention. Viewed from this aspect the invention provides a process for the production of biomass by culturing a microorganism, preferably a methanotrophic bacterium, in an aqueous liquid culture medium circulating in a loop reactor (preferably having an effluent gas removal zone wherefrom carbon dioxide-containing effluent gas is removed from the reactor and upstream thereof a degassing zone in which a driving gas is introduced to drive carbon dioxide in the liquid phase into a separable effluent gas phase and having upstream of said degassing zone a nutrient gas introduction zone in which oxygen and preferably also methane are introduced into the reactor and mixed with the liquid culture medium therein), characterised in that nutrient gas and liquid, culture medium are mixed in said loop reactor by passage through a static mixer comprising a stack of parallel corrugated flexible (and preferably perforated) plates arranged with the stacking direction perpendicular to the direction of flow of said fluid medium and with the corrugation ridges thereof angled to said direction of flow (e.g. at an angle of 20 to 70°, preferably 40 to 50°, especially 45°, relative to the direction of flow) and with their angle to the direction of flow being substantially equal and opposite for adjacent plates.

The stacking direction, i.e. the normal to the surface of a planar sheet placed over either major surface of a mixer plate, may be anywhere between vertical and horizontal. However the stacking direction between successive stacks is preferably rotated through 90°, more preferably 80 to 90°, most preferably about 90°, 0°, 90°, 0° etc. or +45°, −45°, −45° relative to the vertical. Especially preferably the stacking direction for successive stacks is not 0°, 0°, 0° etc. relative to the vertical.

In these last two aspects of the invention, indeed in most aspects of the invention, the loop reactor is preferably one having a centre line, i.e. flow path length, of at least 40 m, more preferably at least 80 m.

Viewed from a further aspect, the invention provides a process for generating biomass by culturing a microorganism in a liquid reaction medium circulating in a loop reactor having an effluent gas-liquid reaction medium separating zone upstream of an effluent gas removal zone, characterized in that oxygen and/or methane is fed into the liquid reaction medium in said separating zone.

Viewed from a further aspect, the invention provides a fermentor apparatus comprising a loop reactor comprising an effluent gas-liquid reaction medium separating zone upstream of an effluent gas removal zone, characterized in that said separating zone has an inlet for feeding oxygen and/or methane into liquid reaction medium therein.

The loop reactor used in the processes of the present invention preferably is one which relies on propulsion rather than gas uplift to move the liquid culture medium around the loop. Since it is easier to maintain nutrient gas and liquid culture medium properly mixed in a substantially horizontal section of the loop, and since mass transfer (i.e. transfer of nutrient gas into the liquid phase) increases with increased pressure in the culture medium, the loop preferably comprises a substantially vertical down-flow zone from the effluent gas removal zone followed by a substantially horizontal (e.g. "U" shaped) zone in turn followed by a substantially vertical up-flow zone leading back to the effluent gas removal zone. In order that degassing and effluent gas/liquid culture medium should be particularly effective, between the substantially vertical up-flow zone and the effluent gas removal zone, it is desirable to have a substantially non-vertical, e.g. horizontal, out-flow zone between the two. This, in which most or all effluent gas/liquid culture medium separation occurs, may have a uniform gradient, may gradually become more horizontal or may change stepwise towards horizontal. The driving gas, i.e. the gas used to displace carbon dioxide from the dissolved phase (usually nitrogen but optionally another inert non-flammable gas) may for example be introduced at one or more points from the beginning of the substantially vertical up-flow zone to the entry into the effluent gas removal zone, however particularly preferably it will be introduced at one or more points between the upper portion (e.g. the upper 20%, more preferably the upper 10%) of the vertical portion of the up-flow zone and the beginning of the flattest (i.e. most horizontal) portion of the out-flow zone. Especially preferably, the driving gas is introduced in the upper portion of the vertical portion of the up-flow zone. In this context it will be understood that the "point" at which a gas may be introduced may have an extended length within the liquid path within the loop, e.g. where gas is introduced through a series of inlet ports or through a multiply perforated inlet port.

In general, where the centre line of the loop, outside the gas effluent removal zone, changes direction, this will be by curvature of the loop rather than by a sharp angled bend so as to improve the flow properties of the liquid culture medium.

The gas pressure in the headspace in the gas effluent removal zone will preferably be from −0.5 to +1.0 atmosphere relative to ambient pressure, especially +0.2 to +0.6. The vertical drop between the gas-liquid surface at the end of the outflow zone and the centre line of the loop in the horizontal zone is preferably at least 10 m, especially at least 18 m, e.g. 18 to 30 m.

The cross sectional area of the loop reactor (outside the gas effluent removal zone) may be constant but preferably is increased at least in the outflow zone, e.g. to a maximum value of at least 2.0 times, more preferably at least 4.0 times that in the minimum cross sectional area part of the down flow and horizontal flow zones (which may typically be before the propeller). Typically, the inner diameters of the loop, outside the gas effluent removal zone may be in the range 30 cm to 3.0 m, especially 1.0 to 2.5 m. Typically also the centre line of the loop, excluding the gas effluent removal zone, has a length in the range 40 to 200 m, preferably 80 to 150 m, preferably with at least 50%, more preferably at least 60%, especially at least 70%, of this in the horizontal zone. The outflow zone preferably has a centre line length of 0.5 to 10 m, especially 1.5 to 8 m.

The loop reactor will generally be circular in cross-section outside the gas removal zone; however in the separation zone other configurations, e.g. rectangular, elliptical or ovoid cross-sections, may be adopted to enhance gas/liquid separation.

Nutrient gas introduction in the loop is preferably effected at least three, more preferably at least six, positions along the length of the loop, preferably with at least 60% being introduced in the horizontal zone. While it is preferred that nutrient gases be introduced in the downflow section, this may require the use of a low cavitation propeller for subsequent propulsion of the liquid culture medium. Such propeller designs are well-known in the field of submarine construction. Typical low-cavitation propellers may have over-lapping blades, or multiple (e.g. at least 6) radially-curved blades (i.e. blades where the base and tip are radially displaced from each other). Unlike in prior reactor designs where nutrient gas input was designed to give a substantially zero dissolved oxygen content in the culture medium by the beginning of the degassing zone, it is desirable to introduce nutrient gases, in particular oxygen, in such amounts that dissolved oxygen content at the beginning of the degassing zone, is at least 3 ppm. To this end, some of the nutrient gas, e.g. up to about 25% of the nutrient gas, is desirably introduced in the upflow zone.

As excess nutrient gas can give rise to toxicity problem for the microorganisms being cultured in the reactor, oxygen introduction is preferably such as to achieve a maximum dissolved oxygen content in the liquid culture medium of no more than 25 ppm, especially no more than 20 ppm, more especially no more than 15 ppm. Likewise to maximise process efficiency in terms of biomass production, methane is preferably introduced in a 1:1 to 1:3, especially 1:1.2 to 1:2.5, more especially about 1:1.8, mole ratio relative to oxygen.

Methane may be used in purified form or in a gas mixture, e.g. natural gas or methane-enriched natural gas. Likewise purified oxygen or oxygen in a gas mixture (e.g. air or oxygen-enriched air) may be used. Where air is used, it is preferably filtered to avoid introduction of toxic impurities.

The methane and oxygen used may likewise be in gaseous (e.g. compressed) or liquefied form; in the latter case however pre-heating will generally be required to prevent the nutrient gas cooling the liquid culture medium unduly.

Natural gas mainly consists of methane, although its composition will vary for different gas fields. Typically, natural gas may be expected to contain about 90% methane, about 5% ethane, about 2% propane and some higher hydrocarbons. During the fermentation of natural gas, methane is oxidized by methanotrophic bacteria to biomass and carbon dioxide. Methanol, formaldehyde and formic acid are metabolic intermediates. Formaldehyde and to some extent carbon dioxide are assimilated into biomass. However, methanotrophic bacteria are unable to use substrates comprising carbon-carbon bonds for growth and the remaining components of natural gas, i.e. ethane, propane and to some extent higher hydrocarbons, are oxidized by methanotrophic bacteria to produce the corresponding carboxylic acids (e.g. ethane is oxidized to acetic acid). Such products can be inhibitory to methanotrophic bacteria and it is therefore important that their concentrations remain low, preferably below 50 mg/l, during the production of the biomass. One solution to this problem is the combined use of one or more heterotrophic bacteria which are able to utilize the metabolites produced by the methanotrophic bacteria. Such bacteria are also capable of utilizing organic material released to the fermentation broth by cell lysis. This is important in order to avoid foam formation and also serves to minimize the risk of the culture being contaminated with undesirable bacteria. A combination of methanotrophic and heterotrophic bacteria results in a stable and high yielding culture.

Besides oxygen and methane, other nutrients, e.g. minerals and a nitrogen source (e.g. ammonia, nitrates, urea, etc.) will generally be added to the liquid culture medium. Unlike oxygen and methane however the degassing operation does not critically affect their concentration and thus their addition can generally each be at only one, two or three points along the loop. For certain minerals, in particular copper, it may however be desirable to effect introduction at a higher number of points along the loop. For copper this is relevant as increased copper concentration serves to increase methane consumption.

Air or pure oxygen may be used for oxygenation and ammonia is preferably used as the nitrogen source. In addition to these nutrients, the bacterial culture will typically require water, phosphate (e.g. as phosphoric acid) and several minerals which may include magnesium, calcium, potassium, iron, copper, zinc, manganese, nickel, cobalt and molybdenum, typically used as sulphates, chlorides or nitrates. All minerals used in the production of the single-cell material should be of food-grade quality.

In the process of the invention it is desirable to monitor carbon dioxide, oxygen and methane content in the effluent gas, and the biomass, nitrogen, dissolved oxygen, phosphate and mineral contents of the culture medium. Biomass content may be measured using samples of the biomass-containing medium extracted for further processing; e.g. by separating biomass from liquid by centrifugation and weighing. Nitrogen, phosphate and mineral contents may also be measured in this extracted material, e.g. using standard procedures, e.g. atomic absorption, etc. Dissolved oxygen content, again measured by standard procedures, is preferably monitored at two or more points about the loop. Effluent gas is preferably sampled and cooled to about 5° C. whereafter oxygen is preferably determined by measuring the paramagnetism of the gas and methane and carbon dioxide by infra-red spectrometry. Typically oxygen content is preferably about 7.5% (v/v), methane content about 4.0% (v/v) and carbon dioxide content about 35% (v/v) when the process is running smoothly.

Ammonia concentration is preferably up to 200 ppm, especially 0.1 to 5 ppm by weight.

Biomass concentration is preferably up to 30 g/L, e.g. 5 to 20 g/L.

Phosphate content in the culture medium is preferably at least 10 ppm by weight so as to minimize foaming at the top of the reactor, especially about 100 to 200 ppm.

Potassium, magnesium and calcium contents in the culture medium are preferably at least 5, 0.5 and 0.5 ppm by weight, especially about 100-200, 20-50 and 20-50 ppm respectively. Copper and iron contents may conveniently be measured in the extracted biomass; preferably their minimum contents are 5 and 200 mg/kg respectively.

During production of the single-cell material, the pH of the fermentation mixture will generally be regulated to between about 5.5 and 7.5, e.g. to 6.5±0.3. Suitable acids/bases for pH regulation may be readily selected by those skilled in the art. Particularly suitable for use in this regard are sodium hydroxide and sulphuric acid. During fermentation the temperature within the fermentor should preferably be maintained to within the range of from 40° C. to 50° C., most preferably 45° C.±2° C.

In operation of the process of the invention, liquid (e.g. some or all of the liquid nutrients, the liquid added to compensate for biomass removal, a fraction of the liquid withdrawn from the reactor, cooled and returned to the reactor to control the temperature, etc.), optionally containing antifoam, is preferably sprayed onto the surface of the liquid culture medium in the degassing zone to reduce foam build up. Likewise, the horizontal flow section of the degassing zone is preferably provided in its upper section with transversely extending baffles to combat foam build up. As a further antifoaming measure, the reactor can be provided in the degassing zone with steam inlets arranged to inject steam into the headspace above the liquid surface.

Any single-cell protein material may be produced in accordance with the processes of the invention. However, preferred microorganisms include bacteria and yeasts. Any bacteria or yeast approved for use in food products may be used and suitable species may be readily selected by those skilled in the art. Particularly preferably, the single-cells for use in the invention will be a microbial culture which consists of methanotrophic bacteria optionally in combination with one or more species of heterotrophic bacteria, especially preferably a combination of methanotrophic and heterotrophic bacteria. As used herein, the term "methanotrophic" encompasses any bacterium which utilizes methane or methanol for growth. The term "heterotrophic" is used for bacteria that utilize organic substrates other than methane or methanol for growth.

While the process of the invention is especially suited to the production of biomass which can be used with relatively little further processing as a feedstuff or food additive, the process may also be used for the preparation of specific chemicals which are generated by the microorganism(s) in the liquid culture medium. In this event, the post-fermentation treatment of the culture medium will involve separation out of the particular chemicals of interest, e.g. by conventional chemical techniques, optionally following lysis of the microorganism cells to release the chemicals of interest. In this embodiment of the invention, microorganisms which naturally produce the chemicals of interest (e.g. proteins, drugs, carotenoids, etc) or which have been genetically modified to produce the chemicals of interest, may be used. Many such microorganisms are known from the literature; however it is particularly preferred to use methanotrophic bacteria.

Preferred bacteria for use in the invention include *Methylococcus capsulatus* (Bath), a thermophilic bacterium originally isolated from the hot springs in Bath, England and deposited as NCIMB 11132 at The National Collections of Industrial and Marine Bacteria, Aberdeen, Scotland. *M. capsulatus* (Bath) has optimum growth at about 45° C., although growth can occur between 37° C. and 52° C. It is a gram-negative, non-motile spherical cell, usually occurring in pairs. The intracellular membranes are arranged as bundles of vesicular discs characteristic of Type I methanotrophs. *M. capsulatus* (Bath) is genetically a very stable organism without known plasmids. It can utilize methane or methanol for growth and ammonia, nitrate or molecular nitrogen as a source of nitrogen for protein synthesis.

Other bacteria suitable for use in the invention include the heterotrophic bacteria *Ralstonia* sp. (formerly *Alcaligenes acidovorans*) DB3 (strain NCIMB 13287), *Brevibacillus agri* (formerly *Bacillus firmus*) DB5 (strain NCIMB 13289) and *Aneurinibacillus* sp. (formerly *Bacillus brevis*) DB4 (strain NCIMB 13288) which each have optimum growth at a temperature of about 45° C.

*Ralstonia* sp. DB3 is a gram-negative, aerobic, motile rod belonging to the family *Pseudomonadaceae* which can use ethanol, acetate, propionate and butyrate for growth. *Aneurinibacillus* sp. DB4 is a gram-negative, endospore-forming, aerobic rod belonging to the genus *Bacillus* which can utilize acetate, D-fructose, D-mannose, ribose and D-tagatose. *Brevibacillus agri* DB5 is a gram-negative, endospore-forming, motile, aerobic rod of the genus *Bacillus* which can utilize acetate, N-acetyl-glucosamine, citrate, gluconate, D-glucose, glycerol and mannitol.

Especially preferred for use in the invention is a microbial culture comprising a combination of the methanotrophic bacterium *Methylococcus capsulatus* (Bath) (strain NCIMB 11132), and the heterotrophic bacteria *Ralstonia* sp. DB3 (strain NCIMB 13287) and *Brevibacillus agri* DB5 (strain NCIMB 13289), optionally in combination with *Aneurinibacillus* sp. DB4 (strain NCIMB 13288). The role of *Ralstonia* sp. DB3 is to utilize acetate and propionate produced by *M. capsulatus* (Bath) from ethane and propane in the natural gas. *Ralstonia* sp. DB3 may account for up to 10%, e.g. about 6 to 8%, of the total cell count of the resulting biomass. The role of *Aneurinibacillus* sp. DB4 and *Brevibacillus agri* DB5 is to utilize lysis products and metabolites in the medium. Typically, *Aneurinibacillus* sp. DB4 and *Brevibacillus agri* DB5 will each account for less than 1% of the cell count during continuous fermentation.

Suitable yeasts for use in the processes of the invention may be selected from the group consisting of *Saccharomyces* and *Candida*.

If desired, the process of the invention may be performed using bacteria (or yeasts) genetically modified so as to generate a desired chemical compound which can then be extracted from the intercellular fluid or the biomass harvested from the reactor. The scientific and patent literature contains numerous examples of such genetically modified microorganisms including, inter alia, methanotrophic bacteria.

In one especially preferred embodiment of the invention, the process is performed using methanotrophic bacteria of the type described in WO 02/18617 to produce carotenoids, e.g. antheraxanthin, adonixanthin, astaxanthin, canthaxanthin, zeaxanthin and the other carotenoids mentioned on pages 39 and 40 of WO 02/18617. To this end, the methanotrophic bacterium Methylomonas 16a (ATCC PTA 2402) may particularly suitably be used. Carotenoids produced in this way may be separated out from the liquid culture medium as described in WO 02/18617, WO 02/20728 and WO 02/20733.

Ideally, the biomass produced from fermentation of natural gas will comprise from 60 to 80% by weight crude protein; from 5 to 20% by weight crude fat; from 3 to 15% by weight ash; from 3 to 15% by weight nucleic acids (RNA and DNA); from 10 to 30 g/kg phosphorus; up to 500 mg/kg iron; and up to 250 mg/kg copper. Particularly preferably, the biomass will comprise from 68 to 73%, e.g. about 70% by weight crude protein; from 9 to 11%, e.g. about 10% by weight crude fat; from 5 to 10%, e.g. about 7% by weight ash; from 8 to 12%, e.g. about 10% by weight nucleic acids (RNA and DNA); from 10 to 25 g/kg phosphorus; up to 310 mg/kg iron; and up to 110 mg/kg copper. The amino acid profile of the protein content should be nutritionally favourable with a high proportion of the more important amino acids cysteine, methionine, threonine, lysine, tryptophan and arginine. Typically these may be present in amounts of about 0.7%, 3.1%, 5.2%, 7.2%, 2.5% and 6.9%, respectively (expressed as a per cent of the total amount of amino acids). Generally the fatty acids will comprise mainly the saturated palmitic acid (approx. 50%) and the monounsaturated palmitoleic acid (approx. 36%). The mineral content of the product will typically comprise high amounts of phosphorus (about 1.5% by weight), potassium (about 0.8% by weight) and magnesium (about 0.2% by weight).

The biomass product of the invention is especially useful as a component or precursor in food products, particularly when used as a substitute for natural plasma in animal feeds and in pet foods. When used in pet foods, additional ingredients may be added to the product such as fats, sugars, salt, flavourings, minerals, etc. The product may then be formed into chunks resembling natural meat chunks in appearance and texture. The product of the invention has the further advantages that this is readily formulated to contain necessary nutrients, is easily digested by the animals and is palatable to the animals.

The product of the invention may find further use as a texturant in meat products (e.g. meat balls), as a replacement for plasma proteins conventionally used as extenders in fresh meat to increase weight and volume, as an emulsifier (e.g. in dressings, etc.), and in bakery products to enhance dough properties.

When used in food products, the biomass, or processed biomass material will typically be used in an amount of from 1 to 10% by weight, preferably up to 5% by weight. The exact proportion will depend on the desired function of the material and can be readily determined by those skilled in the art. Typically, when used as a gelling agent this may be present in an amount of up to 20% by weight, e.g. 5 to 10% by weight (based on dry matter content of the product).

When the reactor was run without meeting the dissolved oxygen content conditions specified above (in particular when overly high dissolved oxygen contents occurred), and when a certain biomass content was reached, although the reactor continued to perform satisfactorily for many hours, relatively suddenly ammonia usage dropped and within a period of only two or three hours the live bacterial population (and hence the biomass content of the material, if it continued to be extracted from the reactor) dropped to virtually zero. While in some cases, immediate cessation of ammonia feed, reduction or cessation of biomass extraction from the reactor and increase or decrease of oxygen feed could "cure" the microorganism population and restore the biomass yield, in many cases this was not sufficient. Investigation of the dead bacteria showed that while these had not lysed the internal organelle structure had been significantly disrupted. This indicated that the bacterial genome was host to hitherto unrecognised viral nucleic acid sequences which under the extraordinary conditions experienced in the reactor were activated to express products which served to shut down normal operation of the cell. It is believed that such genomic prophage rather than plasmid viral infection of monocellular microorganisms has hitherto not been identified and may likewise prove to be problematic in high biomass operation of aerobic loop reactor fermentors, e.g. with bacteria, fungi (e.g. fusarium), yeast or genetically modified cells (e.g. bacterial, mammalian (e.g: human, hamster, mouse, etc.) and it is a further aspect of the invention to use the solutions of the invention relating to the reduction of the dissolved oxygen depleted path length of the reactor in aerobic loop reactor fermentations of bacteria, fungi, yeast or genetically modified cells, e.g. in the production of alcohols (especially methanol or ethanol), foods or food additives or precursors therefor, pharmaceuticals, antibodies, etc.

The rearrangement of the microorganism organelles observed on process malfunction may also be used as a control parameter for feedback control of fermentation reactors in general, and loop reactors in particular, e.g. with observation of organelle rearrangement at all, or above a threshold level, serving to trigger increase in nutrient supply, in particular oxygen and/or methane supply, or to reduce or halt ammonia supply, etc. Such observation could for example be made using flow cytometry on cells removed from an extraction or sampling port in the reactor. This form of feedback control of fermentation reactors forms a further aspect of the invention.

A primary indicator of malfunction in the operation of the processes of the invention is when a depressed pH in the culture medium occurs which recurs despite pH adjustment by base (e.g. NaOH) addition. This appears to be due to formic acid build up or inadequate formic acid to carbon dioxide conversion by the methanotrophic bacteria. An advance warning of this problem could be obtained by monitoring the intracellular formic acid concentration of the bacteria, e.g. by sampling the culture medium, lysing the cells and spectrometrically assaying for formic acid. Where the detected formic acid concentration rises above a preset threshold, preventative action may be taken, e.g. by reducing oxygen and/or ammonia feed rates, etc. Besides intracellular formic acid, extracellular formic acid concentration may be monitored and used as a process control parameter. Likewise dissolved oxygen concentration, dissolved methane concentration and dissolved ammonia concentration may be monitored and used as a process control parameters. Desirably such monitoring is performed on line, i.e. at the reactor, and conventional monitoring apparatus (e.g. spectrometers and the like) may be used. Such monitoring and control forms a further aspect of the invention.

Viewed from a further aspect the invention provides a fermentation reactor adapted for use in one or more processes according to the invention, e.g. by the inclusion of appropriately positioned nutrient gas inlets, low cavitation propellers, stacked plate static mixers, etc.

Viewed from a yet further aspect the invention provides biologically generated products (e.g. biomass, drugs, antibodies, alcohols, etc.) produced by the processes of the invention and their uses, e.g. as, in or as precursors for foodstuffs, as pharmaceuticals, as chemical raw materials, etc.

Where a loop reactor is used for cell culturing, the removal of dissolved carbon dioxide from the culture medium is important and nitrogen is particularly suitable for use in this regard (i.e. as a driving gas as mentioned above).

As a result it is especially beneficial to locate the reactor in the vicinity of (e.g. within 1 km of) an apparatus with a high demand for oxygen, e.g. an alcohol or ethanol production plant, in this way the nitrogen produced in air separation (e.g. liquefication) to produce oxygen for one plant may be used in the fermentor apparatus, together if desired with a small proportion of the oxygen (e.g. as a nutrient gas in the fermentor). Moreover, where the fermentor product is to be dried and, especially where it is oxygen sensitive on drying as is the case with biomass production for bioproteins, the nitrogen may also be used as the drying gas in the spray drier. Such synergistic co-locations of nitrogen/oxygen separator, fermentor and oxygen-demanding plants form a further aspect of the invention.

Where larger scale operation of the process of the invention is desired, it is of course possible simply to increase the dimensions of the reactor and the power of the drive motor. An alternative however is to operate a set of reactors, e.g. arranged radiating out from a central unit housing the degassing zones for all the reactors. One advantage of using a set (e.g. 2, 3, 4 or 5) of reactors is that reaction start-up in one reactor may be effected by inoculation with liquid culture medium from a reactor which is already in operation. Since the reactors generally do have to have down time for cleaning or repair, such an arrangement ensures that operation can be continuous and that the start-up time for the individual reactors may be significantly reduced.

Embodiments of the processes and apparatus of the invention will now be described further with reference. to the accompanying drawings, in which.

Figure 1:
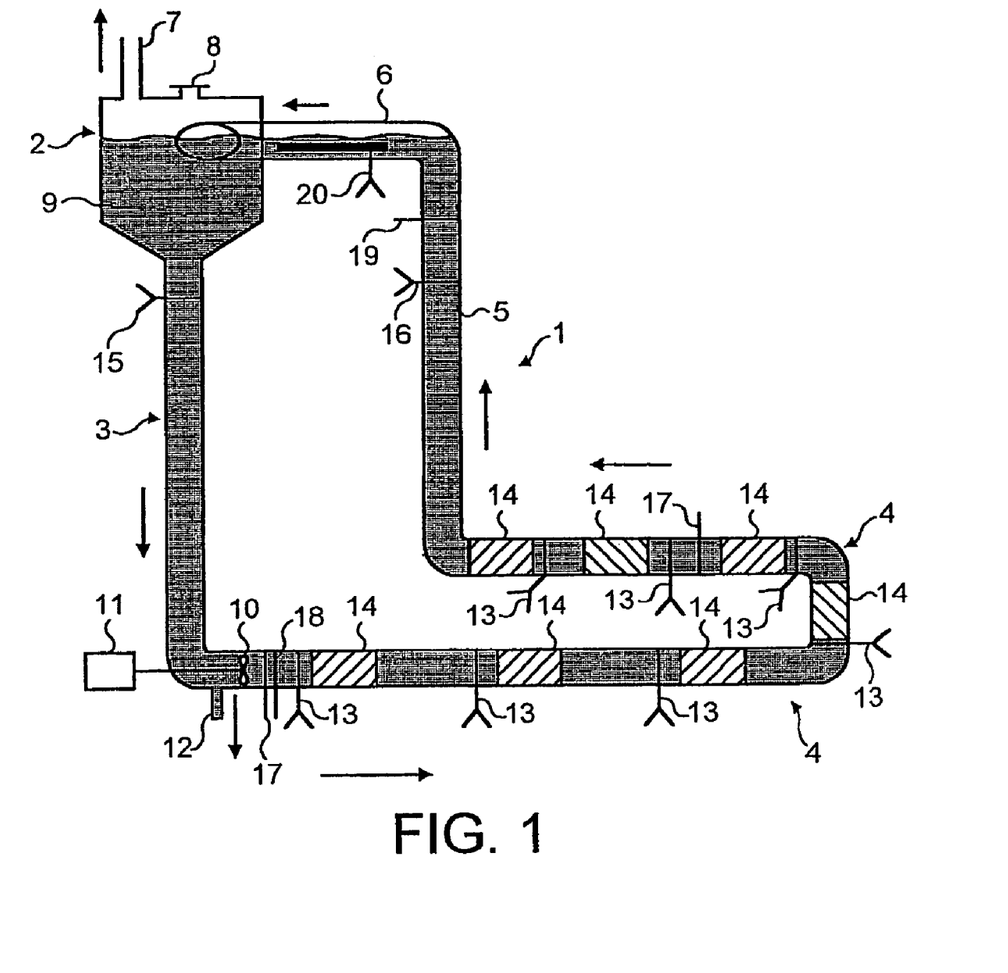
FIG. 1 is a schematic drawing of a loop reactor according to the invention.

Referring to FIG. 1 there is a shown a loop reactor 1, the loop whereof comprises a top unit 2 for effluent gas removal, a vertical down-flow section 3, a horizontal flow section 4, a vertical up-flow section 5, and a horizontal effluent gas/liquid reaction medium separation section 6. Down-flow section 3 is attached to the conical base of cylindrical top unit 2 while separation section 6 enters top unit 2 tangentially at a side so as to achieve cyclonic gas/liquid separation. From the top of top unit 2, effluent gas is removed through outlet port 7. The top of the top unit is also provided with emergency vent 8 which opens automatically if the effluent gas pressure in the top unit exceeds a pre-set maximum, e.g. 0.5 atmosphere above ambient.

The liquid culture medium 9 is circulated round the loop by propeller 10 driven by motor 11 (e.g. a 650 kW motor). Upstream of propeller 10 is exit port 12 from which biomass is removed for dewatering and further processing, e.g. hydrolysis, spray drying etc.

Within the horizontal section 4 of the loop are disposed a series of nutrient gas (e.g. $O_2$ and $CH_4$) inlets 13 (e.g. diffuser plates) and static mixers 14. Nutrient gas inlets 15 and 16 are preferably also provided in the downflow and upflow sections 3 and 5. Ammonia and mineral inlets 17 and 18 and sampling ports are preferably provided around the loop. Monitoring and sampling ports (not shown) are also preferably provided around the loop and in the head space of top unit 2.

Towards the top of upflow section 5 is provided a drive gas (e.g. nitrogen) inlet 19, for example a diffuser plate.

In the base of separation section 6, there is preferably provided a porous diffuser 20 for nutrient gas (especially oxygen) which is elongated along the flow direction so as to supply nutrient gas into the liquid separated out in this section.

Figure 2:
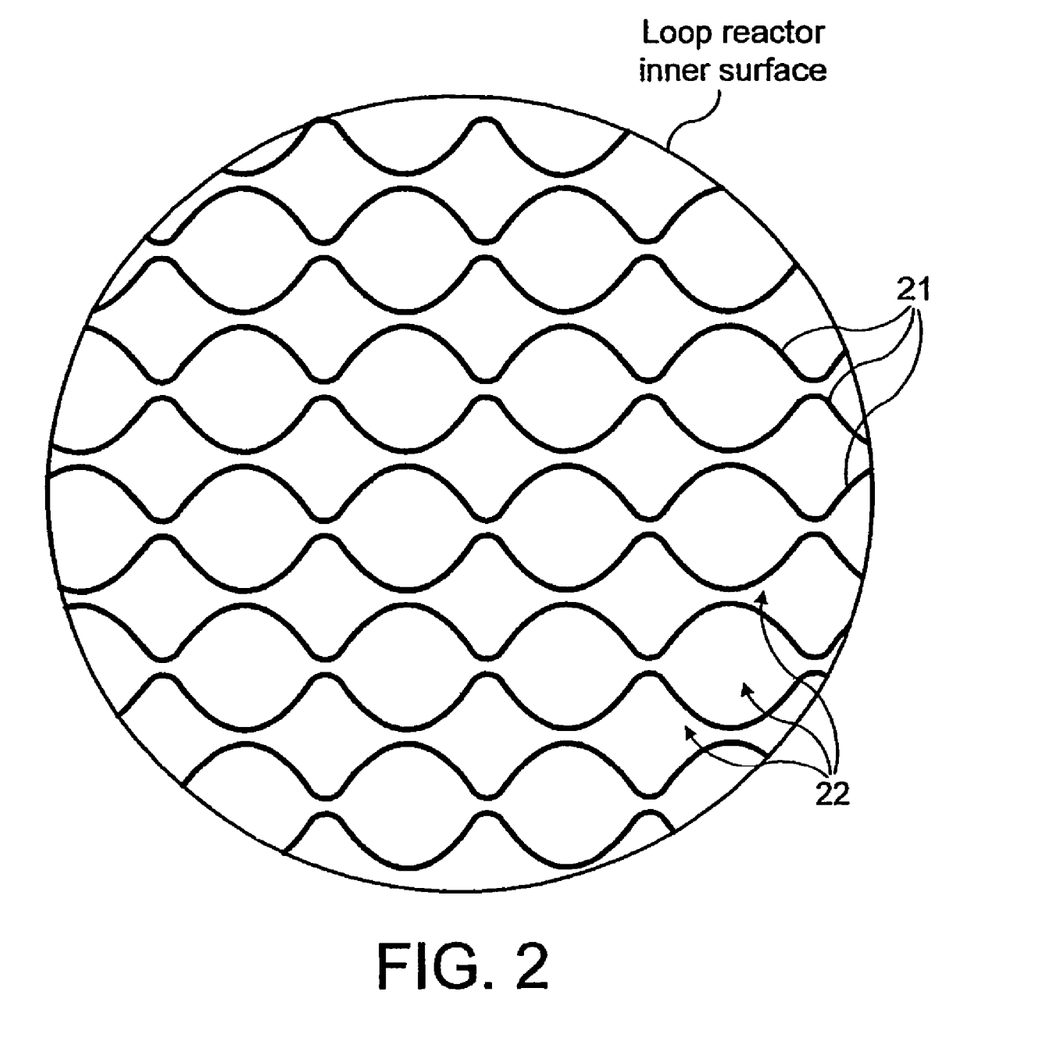
FIG. 2 is a cross section through a horizontal section of the reactor of FIG. 1 showing schematically the arrangement of the plates of the static mixer therein.

Referring to FIG. 2, the loop reactor is shown containing a stack of parallel horizontal corrugated perforated plates 21 disposed one above the other with the corrugations in registry but alternating in direction so as to provide flow channels 22 for the culture medium.

Figure 3:
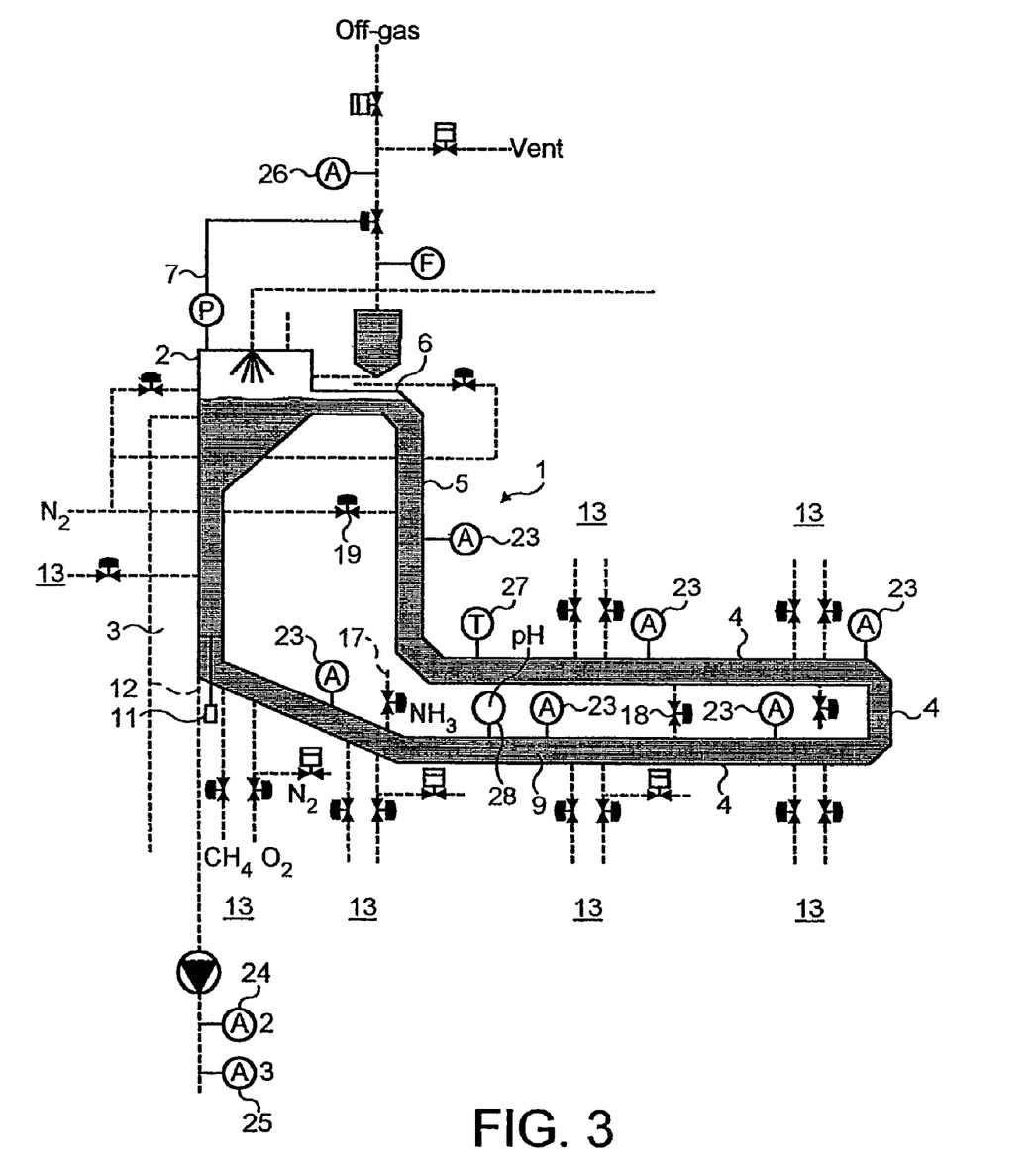
FIG. 3 is a schematic view of a further loop reactor according to the invention.

Referring to FIG. 3 there is a shown a loop reactor 1, the loop whereof comprises a top unit 2 for effluent gas removal, a vertical down-flow section 3, a horizontal flow section 4, a vertical up-flow section 5, and a horizontal effluent gas/liquid reaction medium separation section 6. Down-flow section 3 is attached to the conical base of cylindrical top unit 2 while separation section 6 enters top unit 2 at a side. From the top of top unit 2, effluent gas is removed through outlet port 7. The top of the top unit is also provided with emergency vent which opens automatically if the effluent gas pressure in the top unit exceeds a pre-set maximum, e.g. 0.5 atmosphere above ambient.

The liquid culture medium 9 is circulated round the loop by a propeller driven by a vertically dispersed drive shaft driven by motor (e.g. a 650 kW motor). Upstream of a propeller driven by a vertically disposed drive shaft is exit port 12 from which biomass is removed for dewatering and further processing, e.g. hydrolysis, spray drying etc.

Within the horizontal section 4 of the loop are disposed a series of nutrient gas (e.g. $O_2$ and $CH_4$) inlets 13 (e.g. diffuser plates) and static mixers. Ammonia and mineral inlets 17 and 18 and sampling ports are preferably provided around the loop. Monitoring and sampling ports (not shown) are also preferably provided around the loop and in the head space of top unit 2.

Towards the top of upflow section 5 is provided a drive gas (e.g. nitrogen) inlet 19, for example a diffuser plate.

Dissolved oxygen content is measured by probes 23 within the reactor. Ammonia concentration and cell density are measured by probes 24 and 25 in the harvesting outlet to the reactor, gas composition ($CO_2$, $O_2$, $CH_4$) is measured by probe 26 in the off gas venting line. Temperature and pH are measured within the reactor by probes 27 and 28. The information from these probes is used as a feedback control whereby a yield-optimum gas and ammonia distribution is calculated based on a mechanistic model of the fermentation process providing, repeatedly, optimal settings for the $O_2$, $CH_4$ and $NH_3$ introduction valves, for the diverted flow of culture medium from the reactor into heat exchangers and back into the reactor, and for acid/base dosing to optimise pH.

Figure 4:
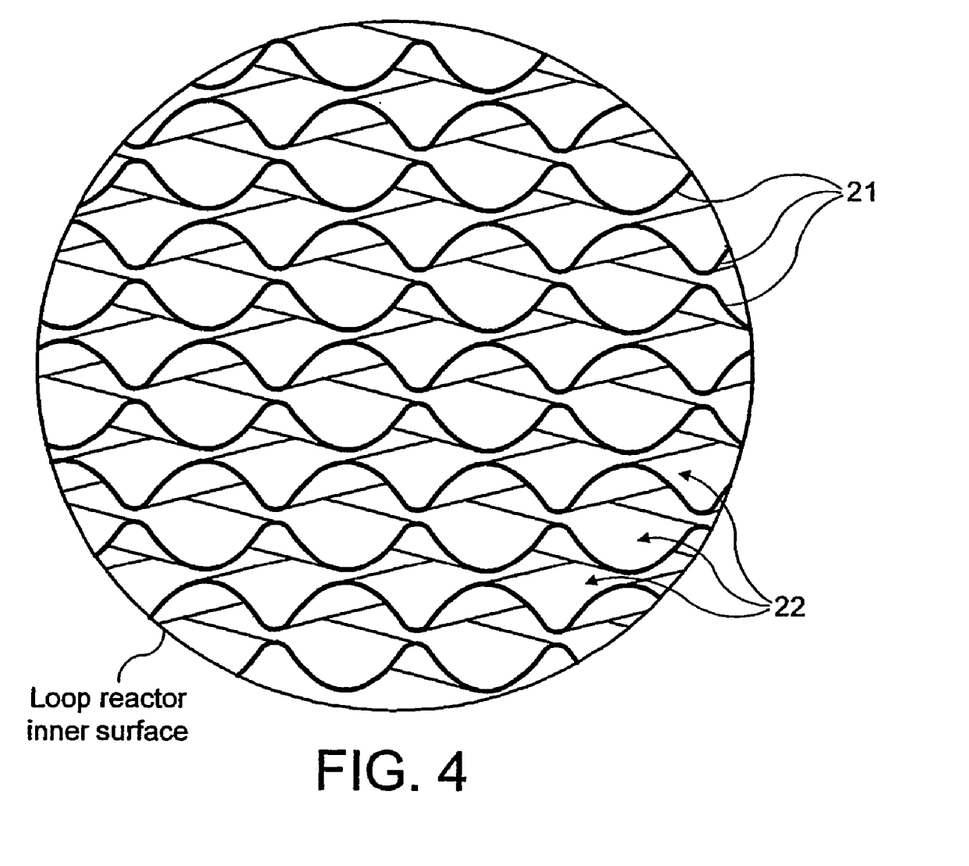
FIG. 4 is a cross section through a horizontal section of the reactor of FIG. 1 or FIG. 3 showing schematically the arrangement of the plates of the static mixer therein.

In FIG. 4 a more preferred mixer array is shown. In this embodiment, the parallel vertical corrugated perforated plates 21 are disposed with their corrugations angled with respect to the flow direction and alternating in orientation.

The mixer plates are preferably flexible as in this way they are self-cleaning. To this end they are conveniently formed from stainless steel of at least 0.2 mm thickness, e.g. about 0.5 to 1.5 mm, especially 0.8 to 1.2 mm thickness. The maximum interplate spacing, i.e. the channel height between corrugations, is preferably at least 25 mm, e.g. 50 to 250 mm, more preferably 80 to 150 mm, especially 90 to 110 mm.

The following non-limiting Example serves further to illustrate the invention.

EXAMPLE 1

Preparation of Homogenized Biomass

A microbial culture comprising *Methylococcus capsulatus* (Bath) (strain NCIMB 11132), *Ralstonia* sp. (formerly *Alcaligenes acidovorans*) DB3 (strain NCIMB 13287) and *Brevibacillus agri* (formerly *Bacillus firmus*) DB5 (strain NCIMB 13289), and optionally and preferably *Aneurinibacillus* sp. DB4 (strain NCIMB 13288) is produced in a loop-type fermentor by continuous aerobic fermentation of natural gas in an ammonium/mineral salts medium (AMS) at 45° C., pH 6.5. The AMS medium contains the following per litre: 10 mg $NH_3$, 75 Mg $H_3PO_4$, 380 mg $MgSO_4.7H_2O$, 100 mg $CaCl_2.2H_2O$, 200 mg $K_2SO_4$, 75 mg $FeSO_4.7H_2O$, 1.0 mg $CuSO_4.5H_2O$, 0.96 mg $ZnSO_4.7H_2O$, 120 µg $CoCl_2.6H_2O$, 48 µg $MnCl_2.4H_2O$, 36 µg $H_3BO_3$, 24 µg $NiCl_2.6H_2O$ and 1.20 µg $NaMoO_4.2H_2O$.

The fermentor is filled with water which has been heat-sterilized at 125° C. for 10 secs. Addition of the different nutrients is regulated according to their consumption. With gradual build-up over time, continuous fermentation is operated with 1-3% biomass (on a dry weight basis).

The biomass is subjected to centrifugation in an industrial continuous centrifuge at 3,000 rpm, optionally followed by homogenization in an industrial homogenizer (pressure drop: 1000 bar (100 MPa); inlet temperature: 15° C. to produce a homogenized biomass), followed by ultrafiltration using membranes having an exclusion size of 200,000 Daltons.

The invention claimed is:

1. A process for the production of biomass comprising:
(A) culturing a microorganism in an aqueous liquid culture medium which circulates in a loop reactor,
wherein said reactor has an effluent gas removal zone where from carbon dioxide-containing effluent gas is removed from the reactor, and
wherein upstream of said an effluent gas removal zone, said reactor has a degassing zone in which a driving gas is introduced to drive and in which carbon dioxide in the liquid phase is driven into a separable effluent gas phase, and
wherein upstream of said degassing zone, said reactor has a nutrient gas introduction zone in which oxygen is introduced into the reactor and mixed with the liquid culture medium therein,
wherein oxygen is introduced at a controlled rate in said nutrient gas introduction zone at a plurality of locations along a loop-reactor flow path through said loop reactor, so as to achieve an average dissolved oxygen content of said liquid culture medium measured using a polarographic oxygen electrode of not greater than 25 parts per million (ppm) by weight; and
(B) harvesting biomass from said reactor.

2. A process for the production of a chemical compound comprising:
(A) culturing a microorganism in an aqueous liquid culture medium which circulates in a loop reactor,
wherein said reactor has an effluent gas removal zone where from carbon dioxide-containing effluent gas is removed from the reactor, and wherein upstream of said an effluent gas removal zone, said reactor has a degassing zone in which a driving gas is introduced and in which carbon dioxide in the liquid phase is driven into a separable effluent gas phase, and wherein upstream of said degassing zone, said reactor has a nutrient gas introduction zone in which oxygen is introduced into the reactor and mixed with the liquid culture medium therein, wherein oxygen is introduced at a controlled rate in said nutrient gas introduction zone at a plurality of locations along a loop-reactor flow path through said loop reactor, so as to achieve an average dissolved oxygen content of said liquid culture medium measured using a polarographic oxygen electrode of not greater than 25 parts per million (ppm) by weight;

(B) harvesting biomass from said reactor; and (C) Separating therefrom a chemical compound produced by said microorganism.

3. The process as claimed in claim 1, wherein said liquid culture medium comprises methanotrophic bacteria, and wherein oxygen and methane are introduced into said reactor and mixed with said liquid culture medium.

4. The process as claimed in claim 1, further comprising separating biomass from a liquid.

5. The process as claimed in claim 1, wherein oxygen is introduced at a controlled rate in said nutrient gas introduction zone at a plurality of locations along the flow path through said loop reactor, so as to achieve an average dissolved oxygen content of said liquid culture medium measured using a polarographic oxygen electrode of not greater than 15 parts per million (ppm) by weight.

6. The process as claimed in claim 1, wherein oxygen is introduced at a controlled rate in said nutrient gas introduction zone at a plurality of locations along the flow path through said loop reactor, so as to achieve a dissolved oxygen content of said liquid culture medium at each said location, with the optional exception of the first said location downstream of said degassing zone, of at least 0.5 parts per million (ppm) by weight.

7. The process as claimed in claim 1, wherein oxygen is introduced at a controlled rate in said nutrient gas introduction zone, so as to achieve: a dissolved oxygen content of the liquid culture medium over at least 30% of the path length of the loop reactor of at least 10 parts per million (ppm) by weight; a dissolved oxygen content of the liquid culture medium immediately prior to introduction of said driving gas in said degassing zone of at least 3 parts per million (ppm) by weight; and an oxygen content of said effluent gas of at least 1 mole %.

8. The process as claimed in claim 1, wherein oxygen is introduced at a controlled rate in said nutrient gas introduction zone, so as to achieve between said nutrient gas introduction zone and said degassing zone a dissolved oxygen content of the liquid culture medium of not less than 3 parts per million (ppm) by weight.

9. The process as claimed in claim 1, wherein oxygen is introduced at a controlled rate into said liquid culture medium, so as to achieve a dissolved oxygen content of said liquid culture medium of not less than 3 parts per million (ppm) by weight over a path length of the loop reactor corresponding to more than 30 seconds.

10. The process as claimed in claim 1, wherein said fluid culture medium is circulated through said loop reactor under the action of a propeller having overlapping or multiple, radially curved blades.

11. The process as claimed in claim 1, wherein nutrient gas and liquid culture medium are mixed in said loop reactor by passage through a static mixer comprising a stack of parallel corrugated flexible plates arranged with the stacking direction perpendicular to the direction of flow of said fluid medium and with the corrugation ridges thereof angled to said direction of flow and with their angle to the direction of flow being substantially equal and opposite for adjacent plates.

12. The process as claimed in claim 1, wherein oxygen is introduced at a controlled rate in said nutrient gas introduction zone, so as to achieve between said nutrient gas introduction zone and said degassing zone a dissolved oxygen content of the liquid culture medium of not less than X ppm by weight, where X is defined by $$X=1.35\,Y.B$$

where B is the biomass content of the culture medium in g/L and Y is from 0.75 to 1.25, and B is 5-30.

13. The process as claimed in claim 1, wherein said loop reactor has a flow path of at least 40 m.

14. The process as claimed in claim 3, wherein said liquid culture medium comprises methanotrophic bacteria, and wherein oxygen and methane are introduced into said reactor at a mole ratio of 1:1 to 3:1, and mixed with said liquid culture medium.

15. The process as claimed in claim 12, wherein B is 10-30.

16. The process as claimed in claim 14, wherein said liquid culture medium comprises methanotrophic bacteria, and wherein oxygen and methane are introduced into said reactor at a mole ratio of 1.2:1 to 2.5:1, and mixed with said liquid culture medium.

17. The process as claimed in claim 15, wherein B is 15-30.

18. The process as claimed in claim 16, wherein said liquid culture medium comprises methanotrophic bacteria, and wherein oxygen and methane are introduced into said reactor at a mole ratio of 1.8:1, and mixed with said liquid culture medium.

19. The process as claimed in claim 17, wherein B is 18-25.

\* \* \* \* \*

UNITED STATES PATENT AND TRADEMARK OFFICE
CERTIFICATE OF CORRECTION

PATENT NO. : 7,579,163 B2
APPLICATION NO. : 10/486694
DATED : August 25, 2009
INVENTOR(S) : Henrik Eriksen, Kurt Strand and Lars Jorgensen It is certified that error appears in the above-identified patent and that said Letters Patent is hereby corrected as shown below:

In claim 1 at column 16, lines 43-47:

delete "wherein upstream of said an effluent gas removal zone, said reactor has a degassing zone in which a driving gas is introduced to drive and in which carbon dioxide in the liquid phase is driven into a separable effluent gas phase, and" and insert --wherein upstream of said effluent gas removal zone, said reactor has a degassing zone in which a driving gas is introduced and in which carbon dioxide in the liquid phase is driven into a separable effluent gas phase, and--

In claim 2 at column 17, lines 1-4:

delete "wherein upstream of said an effluent gas removal zone, said reactor has a degassing zone in which a driving gas is introduced and in which carbon dioxide in the liquid phase is driven into a separable effluent gas, and" and insert --wherein upstream of said effluent gas removal zone, said reactor has a degassing zone in which a driving gas is introduced and in which carbon dioxide in the liquid phase is driven into a separable effluent gas, and--

Signed and Sealed this

Fifth Day of January, 2010

David J. Kappos
*Director of the United States Patent and Trademark Office*